US006626669B2

(12) United States Patent
Zegarelli (10) Patent No.: US 6,626,669 B2
(45) Date of Patent: **\*Sep. 30, 2003**

(54) ORAL THERAPEUTIC DELIVERY APPLIANCE

(76) Inventor: Peter J Zegarelli, 11 Raafenberg Rd., Sleepy Hollow, NY (US) 10591

( * ) Notice: Subject to any disclaimer, the term of this patent is extended or adjusted under 35 U.S.C. 154(b) by 0 days.

This patent is subject to a terminal disclaimer.

(21) Appl. No.: 10/124,110

(22) Filed: Apr. 15, 2002

(65) Prior Publication Data

US 2002/0110780 A1 Aug. 15, 2002

Related U.S. Application Data

(63) Continuation of application No. 09/507,778, filed on Feb. 18, 2000, now Pat. No. 6,386,869.

(51) Int. Cl.[7] .................................................. A61G 5/00
(52) U.S. Cl. ........................................ 433/80; 433/215
(58) Field of Search ............................. 433/215, 80, 6; 424/435, 401

(56) References Cited

U.S. PATENT DOCUMENTS

| | | | |
|---|---|---|---|
| 3,527,218 A | 9/1970 | Westine | 433/80 |
| 3,624,909 A | 12/1971 | Greenberg | 433/80 |
| 4,064,628 A | 12/1977 | Weitzman | 433/25 |
| 4,676,752 A | 6/1987 | Lefkowitz | 433/229 |
| 5,085,585 A | 2/1992 | Zimble | 433/80 |
| 5,129,824 A | 7/1992 | Keller | 433/215 |
| RE34,196 E | 3/1993 | Munro | 433/215 |

(List continued on next page.)

FOREIGN PATENT DOCUMENTS

WO  WO 00 09036  2/2000  ........... A61C/19/06

OTHER PUBLICATIONS

Arakawa, H., et al., "Studies on the techniques of topical application with fluroide gel. 2. Standardization on the amounts of gel applied", *Bulletin of the Kanagawa Dental College*, vol. 17, pp. 3–8, 1989.
Bondestam, O., et al., "Effect of chlorhexidine gel treatment on the prevalence of mutans streptococci and lactobacilli in patients with impaired salivary secretion rate", *SCD Special Care in Dentistry*, vol. 16, pp. 123–127, 1996.
Curtis, J.W., et al., "Assessing the effects of 10 percent carbamide peroxide on oral soft tissues", *The Journal of the American Dental Association*, vol. 127, pp. 1218–1223, 1996.
Epstein, J.B., et al., "Effects of compliance with fluoride gel application on caries and caries risk in patients after radiation therapy for head and neck cancer", *Oral Surgery Oral Medicine Oral Pathology Oral Radiology Endodontics*, vol. 82, pp. 268–275, 1996.
Herman, D.A., "A study of the antimicrobial properties of impression tray adhesives", *The Journal of Prosthetic Dentistry*, vol. 69, pp. 102–105, 1993.

(List continued on next page.)

*Primary Examiner*—Todd E Manahan
(74) *Attorney, Agent, or Firm*—Fish & Neave; William J. McCabe; Bhavana Joneja (57) ABSTRACT

This invention relates to an oral therapeutic delivery appliance. By using this oral therapeutic delivery appliance medicaments may be delivered to oral soft tissues, where medicaments are easily absorbed. To aide the delivery of medicaments to oral soft tissues the oral therapeutic delivery appliance contains a therapeutic pooling reservoir where the medicaments may be placed. The oral therapeutic delivery appliance may be used to treat or aide in the treatment of various oral maladies such as periodontal disease (i.e., gum disease) as well as treating or aiding the treatment of other physical ailments and systemic diseases (e.g., diabetes and other chronic diseases which require either single, intermittent or constant dosing of medicament).

85 Claims, 5 Drawing Sheets

U.S. PATENT DOCUMENTS

| | | | |
|---|---|---|---|
| 5,234,342 A | 8/1993 | Fischer | 433/215 |
| 5,326,685 A | 7/1994 | Gaglio et al. | 433/215 |
| 5,707,235 A | 1/1998 | Knutson | 433/213 |
| 5,842,860 A | 12/1998 | Funt | 433/80 |
| 5,851,512 A | 12/1998 | Fischer | 424/49 |
| 5,895,218 A | 4/1999 | Quinn et al. | 433/80 |
| 5,985,249 A | 11/1999 | Fischer | 424/49 |
| 6,045,811 A | 4/2000 | Dirksing et al. | 424/401 |
| 6,126,443 A | 10/2000 | Burgio | 433/215 |
| 6,247,930 B1 | 6/2001 | Chiang et al. | 433/80 |

OTHER PUBLICATIONS

Jooste, C.H., et al., "The effect of a custom edentulous impression tray on lingual sulcus depth", *The Journal of Prosthetic Dentistry*, vol. 62, pp. 646–651, 1989.

Joyston–Bechal, S., et al., "Caries incidence, mutans streptococci and lactobacilli in irradiated patients during a 12–month preventive programme using chlorhexidine and fluoride", *Journal of the European Organization for Caries Research*, vol. 26, pp. 384–390, 1992.

Meyerowitz, C., et al., "The efficacy of an intraoral fluoride–releasing system in irradiated head and neck cancer patients: a preliminary study", *The Journal of the American Dental Association*, vol. 129, pp. 1252–1259, 1998.

Ostela, I., et al., "Effect of chlorhexidine–sodium fluoride gel applied by tray or by toothbrush on salivary mutans streptococci", *Proceedings of the Finnish Dental Society*, vol. 86, pp. 9–14, 1990.

Padilla, M., et al., "Topical medications for orofacial neuropathic pain: a review", *The Journal of the American Dental Association*, vol. 131, pp. 184–195, 2000.

Render, P.J., "Fabrication of custom trays from existing dentures", *The Journal of Prosthetic Dentistry*, vol. 43, pp. 693–694, 1980.

Ripa, L.W., "An evaluation of the use of professional (operator–applied) topical fluorides", *Journal of Dental Research*, vol. 69, Special Issue, pp. 786–796, 1990.

Tjan, A.H. & Whang S.B., "Comparing effects of tray treatment on the accuracy of dies", *The Journal of Prosthetic Dentistry*, vol. 58, pp. 175–178, 1987.

Venot, M.G., "Simplified blockout material for custom tray fabrication", *The Journal of Prosthetic Dentistry*, vol. 74, pp. 655–656, 1995.

Wang, R.R., et al., "The effect of tray material and surface condition on the shear bond strength of impression materials", *The Journal of Prosthetic Dentistry*, vol. 74, pp. 449–454, 1995.

Wescott, W.B., et al., "Chemical protection against postirradiation dental caries", *Oral Surgery Oral Medicine Oral Pathology with Sections on Endodontics and Dental Radiology*, vol. 40, pp. 709–719, 1975.

ORAL THERAPEUTIC DELIVERY APPLIANCE

CROSS-REFERENCE TO RELATED APPLICATION

This application is a continuation of U.S. patent application Ser. No. 09/507,778, filed Feb. 18, 2000 (now U.S. Pat. No. 6,386,869).

This invention relates to a dental medical oral appliance, and more specifically a drug delivery device for the administration of medicaments orally by means of this appliance. This invention also relates to the methods for treating various oral maladies such as periodontal disease (i.e., gum disease) as well as treating other physical ailments and systemic diseases (e.g., diabetes and other chronic diseases which require either single, intermittent or constant dosing of medicament).

BACKGROUND OF THE INVENTION

Dental appliances or dental trays have been used in various dental procedures for many years. For example, dental appliances have been used to whiten teeth (See U.S. Pat. No. Re. 34,196 to Munro). Or, dental appliances (referred to as night guards)have been used to prevent patients from grinding their teeth while asleep. They have also been used in conjunction with fluoride as a caries (cavity) preventative. And, dental appliances in conjunction with medication have been used to treat oral pain. (See M. Padilla, C. T. Glenn and M. L. Robert, *Topical medications for orofacial neuropathic pain*: a review, 131 Journal of the American Dental Association 185 (February 2000).

A general process for preparing these dental appliances is by forming an alginate impression which registers all teeth surfaces in a jaw. Next, a stone cast model is made using the alginate impression of the mouth. In the case of tooth whitening agents, the reservoirs for holding whitening agents are formed by building a layer of rigid material on the teeth surface(s) to be treated of the stone cast (See U.S. Pat. No. 5,985,249).

A dental tray is then vacuum formed from the cast using conventional techniques. Once formed, the tray is trimmed just at the gingival margin on both the buccal and lingual surfaces. The resulting tray provides a perfect fit of the patient's teeth with pooling reservoirs at the teeth surfaces to be treated.

A disadvantage with the current dental appliances is that these dental appliances deliver compositions to (and thereby treat) only the hard tissues (i.e., teeth) and not to the soft tissues (i.e., periodontium or gums). It is well documented that oral soft tissues readily absorb all types of substances, e.g. nitroglycerine to treat angina. These old dental appliances are limited to treating the patient's teeth.

SUMMARY OF THE INVENTION

In view of the forgoing, it is an object of this invention to provide an oral appliance and drug delivery device that predominantly delivers compositions to the gingival and soft tissues of the mouth.

It is another object of this invention to provide methods and the apparatus for treating oral maladies as well as other physical ailments and systemic diseases.

These and other objects of the invention are accomplished in accordance with the principles of the invention by providing a delivery appliance that extends to the muco-gingival junction. It is maintained that the oral therapeutic delivery appliance would also be effective if it were to be extended beyond to the muco-buccal fold or short of the muco-gingival junction, but would be most effective and comfortable at the muco-gingival junction.

Furthermore, the oral therapeutic delivery appliance contains a therapeutic pooling reservoir at the gingival margin. Once the medicament is placed in the oral therapeutic delivery appliance and the appliance is placed in the patient's mouth, the medicament will be forced to settle in the therapeutic pooling reservoir due to the snug fit of the appliance to the teeth and the muco-gingiva. As used herein the term medicament includes all medicaments, medicinals and pharmacological agents.

The oral therapeutic delivery appliance stays in the mouth not only mechanically by locking itself about the teeth and soft tissues but also by the suction created by the saliva and the medicament. The tight fit of the oral therapeutic delivery appliance further forces the medicament not only to pool at the gingival margin but also to compress it and force it into the gingival sulcus and into the periodontal pockets. This is precisely where active periodontal disease is and where the medicament will be delivered. It is also an area with tremendous capillary blood flow and absorption.

Further features of the invention, it's nature and various advantages will be more apparent when viewing the accompanying drawings and the following detailed descriptions of the preferred embodiments.

DETAILED DESCRIPTION OF THE PREFERRED EMBODIMENTS

As summarized above, the present invention generally relates to a delivery appliance, and more particularly to the administration of medicaments by means of this appliance. This invention also relates to methods and apparatus for treating oral maladies as well as other physical ailments and systemic diseases (e.g., gum disease, diabetes, etc.).

Figure 1:
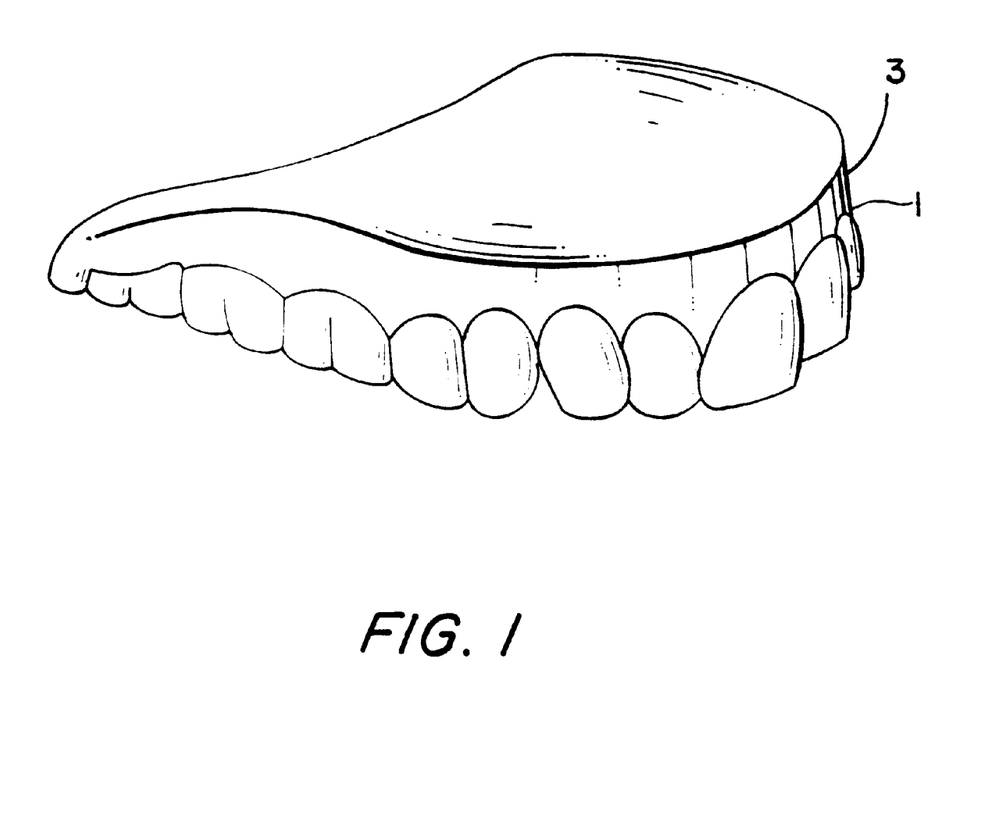
FIG. 1 is a simplified perspective view of an illustrative embodiment of a stone cast of a patient's mouth.
Figure 2:
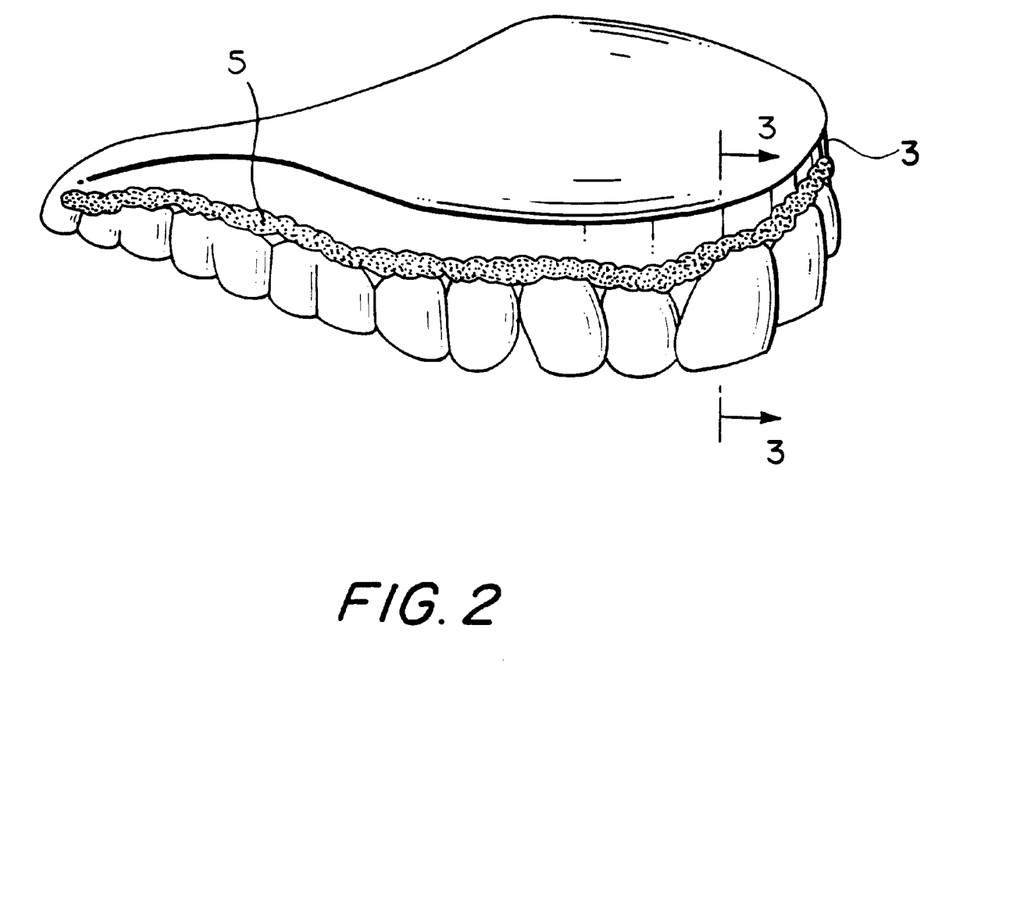
FIG. 2 is a simplified perspective view of an illustrative embodiment of a stone cast of a patient's mouth with a composite applied at the soft tissue at or near the gingival margin.

The illustrative embodiment in FIGS. 1 and 2 show a solid stone cast model of a patient's mouth with bead 5 of flowable composite placed at or near the gingival margin 1 area, henceforth referred to as the junctional therapeutic zone (JTZ).

Any method known in the art may be used to form the solid stone cast of patient's mouth (see U.S. Pat. No. 5,985,249) and for taking an impression of the upper and/or lower jaws. For the present invention care must be taken not only to register the hard tissues (i.e., teeth) but also the adjacent soft tissue areas buccally, lingually and palatally. All gingival areas to be treated should be included in this impression. Preferably, the impression should extend at least up to 5 mm beyond the gingival margin 1 onto the soft tissues and preferably to the muco-gingival junction 3. More preferably, the impression should extend beyond the muco-gingival junction. Next, dental stone is poured into the dental impression and a solid stone cast model is fabricated. This model is then trimmed and prepared for forming the oral therapeutic delivery appliance 4.

To prepare the stone cast model of the patient's mouth for fabricating the oral therapeutic delivery appliance 4, bead 5 of flowable composite is added at the gingival margin 1. The preferred placement of flowable composite 5 is 1, the JTZ. The JTZ encompasses both the tooth at the gingival margin and the gingiva at the gingival margin.

The preferred flowable composite 5 placed at the JTZ on the stone cast and used to form therapeutic pooling reservoir 20 is a gel like viscous paste sold under the trademark Flow-it by Jeneric Pentron Inc. Other similar composites by alternate manufacturers may also be used. Flowable composite 5 is then light-cured solid with a standard curing light found in the art. Other materials that may be applied at the JTZ of the stone cast to create therapeutic pooling reservoir 20 include, but are not limited to, high melting waxes, modeling clay, acrylics or other polymerizable materials. The material placed at the JTZ of the stone cast to form therapeutic pooling reservoir 20 should be of sufficient width and depth to cover the JTZ of all the periodontal areas to be treated both buccally and lingually, and to form a therapeutic pooling reservoir of sufficient size to hold the dose of medicament to be delivered via the oral therapeutic delivery appliance 4. Furthermore, this material should follow the contours of the gingival margin along the dental papillae, into furcations, interproximal areas and cols and onto the teeth along the gingival margins. The volume of the material used on the JTZ to form therapeutic pooling reservoir 20 should be similar to the volume of the medicament to be delivered. The preferred width of flowable composite 5 added at the JTZ of the stone cast is from at least about 1 mm to about 5 mm; flowable composite 5 forms a corresponding therapeutic pooling reservoir on the oral therapeutic delivery appliance 4 of a width of about 1 mm to about 5 mm. The preferred thickness of flowable composite 5 at the JTZ is about 1 mm to about 3 mm; flowable composite 5 forms a corresponding therapeutic pooling reservoir on the oral therapeutic delivery appliance 4 of a depth of about 1 mm to about 3 mm. Variations from these ideals will still provide an efficacious result. To better assure that therapeutic pooling reservoir 20 is of an appropriate size to deliver the dose of medicament that the patient may need, it is suggested that a precise volume of flowable composite 5 be placed into a calibrated syringe and applied at the JTZ of the stone cast so that when therapeutic pooling reservoir 20 is formed it is able to hold a medicament of similar volume.

Figure 5:
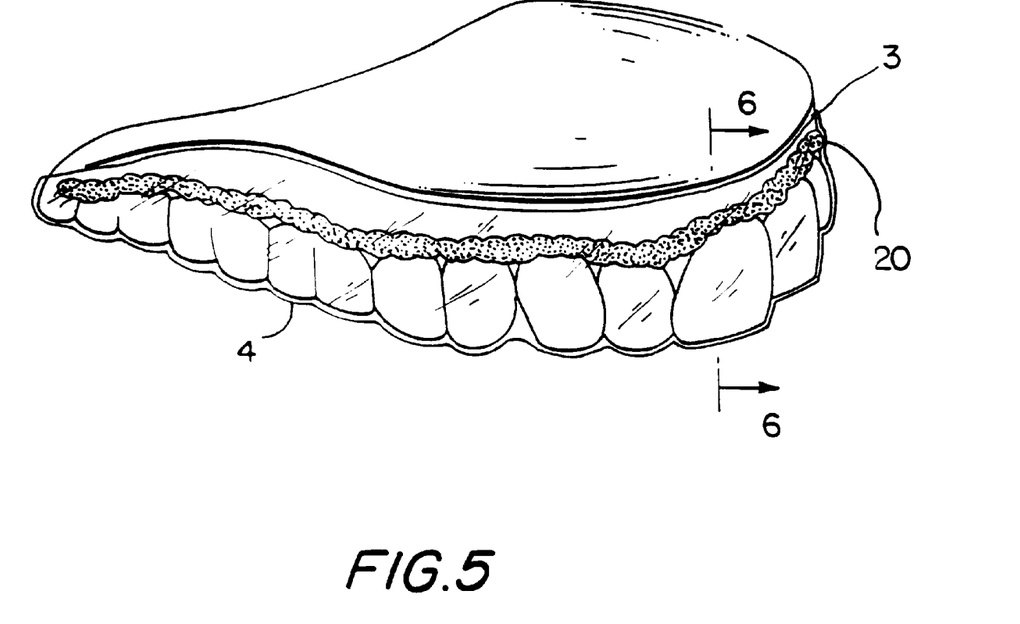
FIG. 5 is a simplified perspective view of FIG. 4.
Figure 6:
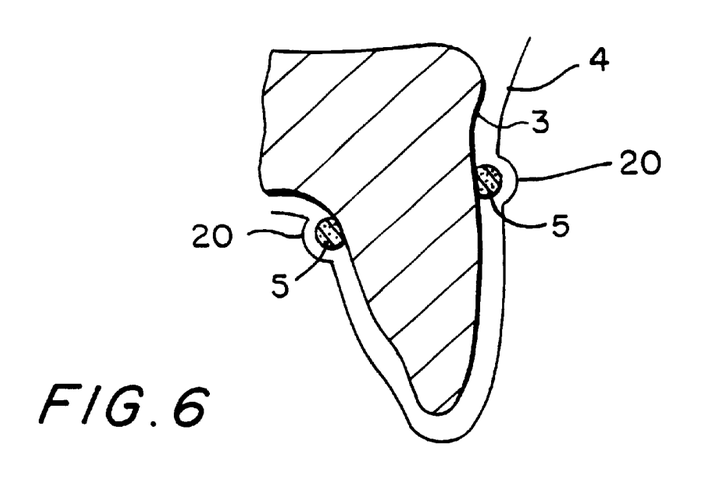
FIG. 6 is a simplified cross-sectional view along line 6—6 of FIG. 5.
Figure 7:
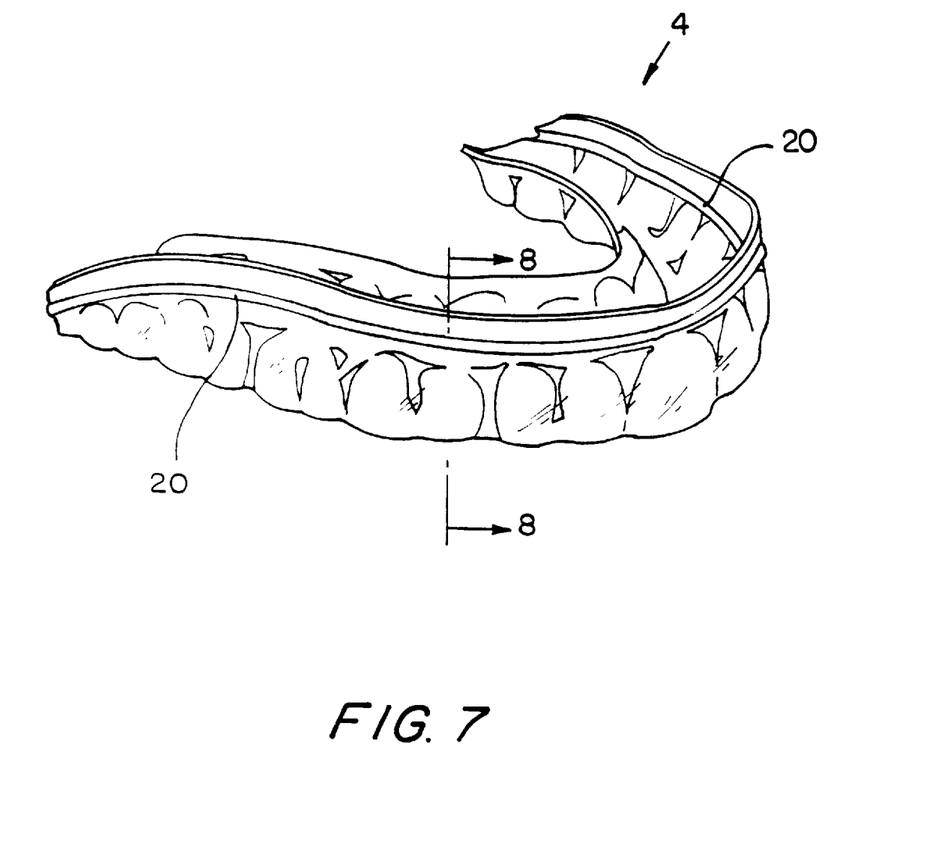
FIG. 7 is a simplified perspective view of the oral therapeutic delivery appliance.
Figure 8:
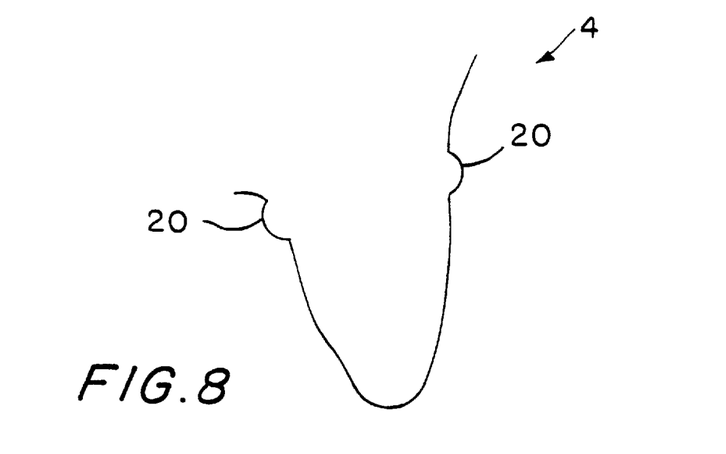
FIG. 8 is a simplified cross-sectional view along line 8—8 of FIG. 7.

Flowable composite 5 may be placed at the JTZ of the stone cast so that it forms therapeutic pooling reservoir 20 around the entire mouth as shown in FIG. 5. Or, alternatively, flowable composite 5 may be placed on the stone cast at specific areas of the JTZ when localized treatment is required.

Figure 3:
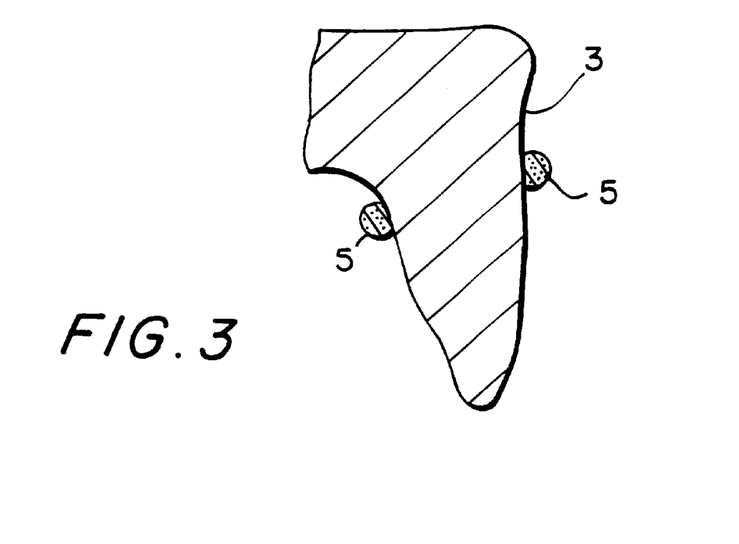
FIG. 3 is a simplified cross-sectional view along line 3—3 of the stone cast shown in FIG. 2.
Figure 4:
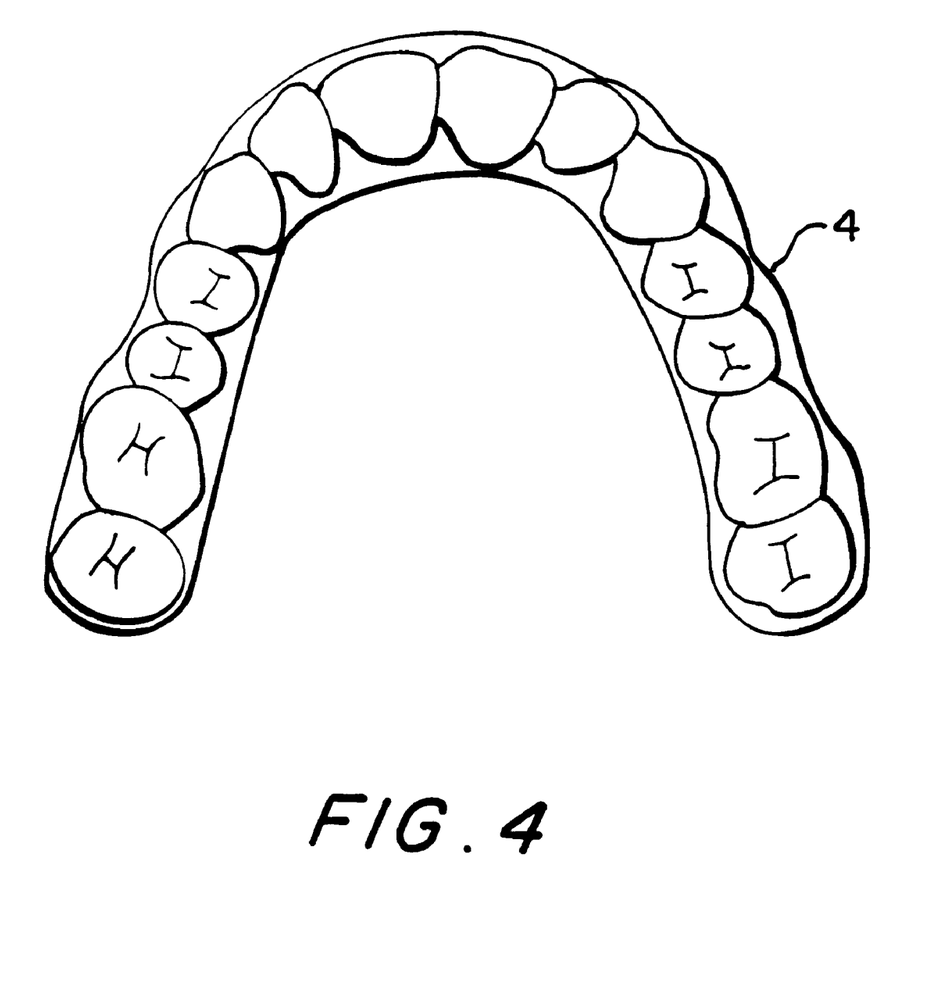
FIG. 4 is a simplified top view of the stone cast with a oral therapeutic delivery appliance formed over the cast and trimmed near the muco-gingival junction.

To form the oral therapeutic delivery appliance 4 of FIG. 3, a standard thermoplastic sheet is molded about the stone cast. The thermoplastic sheet may be heat softened and vacuum wrapped about the stone cast model of FIG. 1. The thermoplastic sheet may vary in thickness from about 0.04 inches to about 0.2 inches depending on the stiffness of the appliance 4 desired. The preferred thickness of the thermoplastic sheet is about 0.06 inches. The thermoplastic sheet may be either rigid or flexible. Such sheets are available from various suppliers (e.g., Dental Resources Inc.). The thermoplastic sheet is then heat softened and vacuum wrapped (vacuum former manufactured by Buffalo Dental, Inc and others) about the stone cast so that it forms a very tight fitting thermoplastic wrap delivery appliance 4. Various other types of standard appliance materials may be used according to the patient's comfort.

The oral therapeutic delivery appliance 4 is next removed from the stone cast model and trimmed. In order to maximize the delivery of the medicaments that will be used in conjunction with this delivery appliance 4 and to obtain a secure seal, the oral therapeutic delivery appliance 4 is trimmed well beyond the JTZ therapeutic pooling reservoir. Ideally, it is trimmed at the muco-gingival junction, however, it can be trimmed either longer or shorter to the muco-gingival junction. It is maintained that the oral therapeutic delivery appliance 4 would be effective without the JTZ therapeutic pooling reservoir, but less so.

The oral therapeutic delivery appliance 4 may cover the hard palate. Here the oral therapeutic delivery appliance 4 can be trimmed approximately 5 mm from the JTZ or alternatively the entire hard palate can remain covered much like a full upper denture.

As a result of the custom fit, the oral therapeutic delivery appliance 4 will remain in the mouth so that the medicament remains in contact with the gums due to mechanical pressure and without the aid of any auxiliary adhesive agents, such as xanthan gum and polyols. Furthermore, therapeutic pooling reservoir 20 formed by 5 on the oral therapeutic delivery appliance 4 may be distinguished and highlighted from the rest of the appliance 4 in order to assist the patient in the proper placement of the medicament by outlining the therapeutic pooling reservoir with a simple ball point pen or indelible marker.

The preferred method of placing the medicament in the oral therapeutic delivery appliance 4 is via a calibrated syringe. This syringe will contain the precise amount of medicament that the patient requires for his specific ailment. Other systems, such as tubes or vials containing the medicament may also be used. The medicament need not be placed precisely at the therapeutic pooling reservoir 20, since the snug fit of the oral therapeutic delivery appliance 4 about the adjacent teeth and gums will force the majority of the medicament to settle in the therapeutic pooling reservoir 20 and force the agent into the gingival sulcus and periodontal pockets. Here, the soft tissues will readily absorb the medicaments and the hard tissues (teeth) will also be coated and treated.

The oral therapeutic delivery appliance 4 may be used to treat a variety of ailments. For example, antibiotics and/or antimicrobials may be added to the oral therapeutic delivery appliance 4 in order to treat or aide in the treatment of gum disease. Currently, the dental practitioner places impregnated cords, injectable medicaments or dissolvable chips under the gums to treat gum diseases. These treatments require a dental visit, take time, can only treat a limited area and are most often uncomfortable and painful not only during the procedure but also post-operatively. Oral rinses and toothpastes as well are used presently to treat gum disease. They suffer from the drawback that they are in contact with the gums for only a short time and become diluted by the saliva and are quickly expectorated. Also, home appliances such as the Water-Pik are used to treat gum disease, but they suffer from the same drawbacks as the rinses and are sloppy and cumbersome to use. Both home appliances and oral rinses also can not readily deliver the medicaments consistently into the gingival sulcus and gum pockets where the disease is located. With the present invention, the medicament may be in contact with the patient's gums for as long as needed for the appropriate treatment and the medicament will suffer little or no dilution by the patient's saliva. For example, the medicament may be in contact with the patient's gums for several minutes to several hours to overnight and in the comfort of the patient's home. The oral therapeutic delivery appliance 4 is comfortable, easy to place and easy to remove. When finished with the treatment, the patient may expectorate and/or rinse to flush the medicament from his mouth (unlike U.S. Pat. No. 5,985,249, whose medicament is not dissolvable in saliva).

The oral therapeutic delivery appliance 4 may also be used to administer anesthetics. Currently, dentists administer anesthetics via oral injections or with the application of a topical anesthetic. The injections are uncomfortable and painful. The topical anesthetic is placed by the practitioner on the desired location for usually an inadequately short time and is quickly diluted by the saliva. With the use of the present invention, anesthetics may be self administered (i.e., by the patient) pre-operatively comfortably and painlessly by placing them in the oral therapeutic delivery appliance 4 prior to the dental visit. Upon reaching the dental office the patient is adequately anesthetized for procedures such as periodontal scaling and root planing, impressions for crown and bridge, injections, minor surgical procedures and others. Conversely, the oral therapeutic delivery appliance 4 may-also be used post-operatively to reduce pain by placing the anesthetic at the surgical site.

Further applications include but are not limited to the use of steroids, antibiotics, analgesics and antimicrobials for the post-operative healing of surgical sites such as third molar (wisdom teeth) extractions, periodontal surgery, implant placement and others. Here, the therapeutic pooling reservoir of the oral therapeutic delivery appliance 4 will be placed at the anticipated surgical site.

There are various oral dermatologic diseases such as lichen planus and desquamative gingivitis which respond to various therapies such as the topical application of steroids. Previously, dilution was always a problem as was the ability of the medicament to stay at the site of the lesion for any period of time. With the oral therapeutic delivery appliance 4 a therapeutic pooling reservoir can be customized to treat the specific sites of the lesions on the palate, the attached gingiva or the adjacent soft tissues.

Patients undergoing head and neck radiation treatment for cancer often suffer from high incidences of dental caries because of xerostomia (dry mouth). Xerostomia may also be caused by salivary gland disease, various medications and other causes. The topical application of fluorides helps to prevent root caries where they typically form (i.e., gingivally and sub-gingivally) at the area of the JTZ. Fluoride and other medicaments may also be used to treat root sensitivity and post-periodontal surgical sensitivity by administering them via the oral therapeutic delivery appliance 4.

Applications of anti-plaque agents to combat the flora of periodontal disease and gingivitis may be added to the oral therapeutic delivery. These include but are not limited to chlorhexidine, fluoride, metronidazole, minocycline, tetracycline and peroxide.

Applications to reduce or relieve pain may also be added to the oral therapeutic delivery appliance. These include but are not limited to lidocaine and benzocaine.

Applications of anti-virals such as Zovirax to treat Acute Herpetic Gingivo-Stomatitis among other oral conditions may now be easily applied to the gums topically via the present invention by extending the therapeutic pooling therapeutic pooling reservoir to include the entire zone of attached gingiva and the palate.

The oral therapeutic delivery appliance 4 may be used by patients who are undergoing chemotherapy or who are otherwise immunocompromised (e.g., HIV), or with low platelet and/or white blood cell counts and who suffer from generalized oral infections, the use of chlorhexidine, anesthetics, antibiotics, antifungals, antivirals and others are indicated. Here, and in other uses, the therapeutic pooling reservoir of the oral therapeutic delivery appliance 4 can be extended to cover all soft tissues to be treated.

The oral therapeutic delivery appliance 4 also may be used for other physical ailments and systemic diseases that include but are not limited to those diseases which require a daily dosing of medication. It is possible to treat diabetes with absorbable insulin which will give a more even administration of drug instead of the injection which gives a large bolus at one time. Chemo-therapeutic agents, hypertensive and cardiac medications, long dosage administration of antibiotics and other pharmacotherapeutic agents can also be administered via the oral therapeutic delivery appliance 4.

Applications for antibiotic prophylaxis for mitral valve prolapse and other conditions may now be accomplished with the oral therapeutic delivery appliance by placing an antibiotic and/or antimicrobial in the oral therapeutic delivery appliance pre-operatively. Currently, patient's ingest large doses of systematic antibiotics pre-operatively. With the use of the oral therapeutic delivery appliance 4 antibiotic doses may be reduced and antibiotics may be applied to the precise area where treatment is needed.

Also, applications for antibiotics and/or antimicrobials to treat Acute Necrotizing Ulcerative Gingivitis may now be accomplished by placing medicaments into the oral therapeutic deliver appliance 4 instead of taking systematic antibiotics and/or rinsing with hydrogen peroxide.

The oral therapeutic delivery appliance 4 allows the patient to self administer a wide variety of medicaments comfortably, painlessly and in the convenience of their own home.

It will be understood that the foregoing is only illustrative of the principles of this invention and that various modifications can be made by those skilled in the art without departing from the scope and spirit of the invention.

What is claimed is:

1. An oral therapeutic appliance for delivering medicament to a patient's oral soft tissue, the appliance being formed from a sheet material molded to fit contours of at least a portion of the patient's teeth, edentulous areas or both, and adjacent buccal and lingual soft tissues, the appliance comprising one or more pooling reservoirs for holding a precise volume of medicament to be delivered to the oral soft tissue, said reservoirs located on the appliance corresponding to the oral soft tissue of the patient's mouth, wherein said one or more pooling reservoirs allow movement of said medicament.

2. The oral therapeutic appliance of claim 1, wherein the medicament to be delivered is selected from the group consisting of antibiotic compounds, antimicrobial compounds, antiviral compounds antifungal compounds, anesthetic compounds, analgesic compounds, steroids and combinations thereof.

3. The oral therapeutic appliance of claim 2, wherein the antibiotic compound to be delivered comprises tetracycline.

4. The oral therapeutic appliance of claim 2, wherein the antimicrobial compound to be delivered comprises chlorhexidine.

5. The oral therapeutic appliance of claim 1, wherein the medicament to be delivered is insulin, chlorhexidine, fluoride, metronidazole, minocycline, tetracycline, peroxide, or combinations thereof.

6. The oral therapeutic appliance of claim 1, wherein the pooling reservoirs are located on the oral therapeutic appliance corresponding to the oral soft tissue at or near a patient's gingival margin.

7. The oral therapeutic appliance of claim 6, wherein at least one of the pooling reservoirs has a depth of from about 1 mm to about 3 mm.

8. The oral therapeutic appliance of claim 1, wherein the pooling reservoirs are located on the oral therapeutic appliance corresponding to the oral soft tissue at or near the patient's palate.

9. The oral therapeutic appliance of claim 1, wherein the pooling reservoirs are located on the oral therapeutic appliance corresponding to the patient's sublingual oral soft tissue.

10. The oral therapeutic appliance of claim 1, wherein the pooling reservoirs are located on the oral therapeutic appliance corresponding to the oral soft tissue at or near the patient's palate and to the patient's sublingual oral soft tissue.

11. The oral therapeutic appliance of claim 1, wherein at least one of the pooling reservoirs has a width of from about 1 mm to about 5 mm.

12. The oral therapeutic appliance of claim 2, wherein at least one of the pooling reservoirs at the oral soft tissue extends substantially the length of the gingival margin where the medicament is to be delivered.

13. The oral therapeutic appliance of claim 1, wherein the sheet material is a thermoplastic sheet.

14. The oral therapeutic appliance of claim 13, wherein the thermoplastic sheet has a thickness of from about 0.04 inches to about 0.2 inches.

15. The oral therapeutic appliance of claim 14, wherein the thermoplastic sheet has a thickness of about 0.06 inches.

16. The oral therapeutic appliance of claim 13, wherein at least a portion of the molded sheet material extends to the patient's muco-gingival junction.

17. The oral therapeutic appliance of claim 1, wherein at least a portion of the molded sheet material extends at least 2 mm beyond the patient's gingival margin.

18. The oral therapeutic appliance of claim 1, wherein at least a portion of the molded sheet material extends at least 2 mm buccally beyond the patient's gingival margin.

19. The oral therapeutic appliance of claim 1, wherein at least a portion of the molded sheet material extends at least 2 mm lingually beyond the patient's gingival margin.

20. The oral therapeutic appliance of claim 1, wherein at least a portion of the molded sheet material extends at least 5 mm beyond the patient's gingival margin.

21. The oral therapeutic appliance of claim 1, wherein at least a portion of the molded sheet material extends at least 5 mm buccally beyond the patient's gingival margin.

22. The oral therapeutic appliance of claim 1, wherein at least a portion of the molded sheet material extends at least 5 mm lingually beyond the patient's gingival margin.

23. A method of delivering medicament to a patient's oral soft tissue comprising:
    (a) covering at least a portion of the patient's teeth, edentulous areas or both, and adjacent buccal and lingual soft tissues with a molded contoured oral therapeutic appliance that is configured to extend beyond the patient's gingival margin, the oral therapeutic appliance further comprising one or more pooling reservoirs for holding a precise volume of medicament to be delivered to the oral soft tissue, said reservoirs located on the oral therapeutic appliance corresponding to the soft tissue at or near the gingival margin for holding medicament, wherein said one or more pooling reservoirs allow movement of said medicament;
    (b) placing the medicament to be delivered within the oral therapeutic delivery appliance;
    (c) positioning the oral therapeutic appliance over the teeth, edentulous areas or both in the area where the medicament is to be delivered such that at least a portion of the medicament within one or more of the pooling reservoirs is able to contact the soft tissue; and
    (d) maintaining the oral therapeutic appliance in position for a sufficient time to allow a therapeutically effective amount of the medicament to be absorbed by the soft tissue.

24. The method of claim 23, wherein at least one of the pooling reservoirs has a width of from about 1 mm to about 5 mm.

25. The method of claim 23, wherein at least one of the pooling reservoirs has a depth of from about 1 mm to about 3 mm.

26. The method of claim 23, wherein the precise volume of medicament is placed in the pooling reservoir via a syringe or other calibrated instrument.

27. The method of claim 23, wherein the oral therapeutic appliance is maintained in position primarily due to a tight fit.

28. The method of claim 23, wherein a majority of the medicament to be delivered is located within at least one or more of the pooling reservoirs.

29. The method of claim 23, wherein the medicament to be delivered is selected from the group consisting of antibiotic compounds, antimicrobial compounds, antiviral compounds, antifungal compounds, anesthetic compounds, steroids and combinations thereof.

30. The method of claim 29, wherein the antibiotic compound to be delivered comprises tetracycline.

31. The method of claim 29 wherein the antimicrobial compound to be delivered comprises chlorhexidine.

32. The method of claim 23, wherein the medicament to be delivered is insulin, chlorhexidine, fluoride, metronidazole, minocycline, tetracycline, peroxide, or combinations thereof.

33. An oral therapeutic appliance comprising one or more pooling reservoirs for delivering a precise volume of medicament to a patient's oral soft tissue, wherein said one or more pooling reservoirs allow movement of said medicament, the appliance being formed from a sheet material molded to fit contours of at least a portion of the patient's teeth, edentulous areas or both, and adjacent buccal and lingual soft tissues.

34. The oral therapeutic appliance of claim 33 wherein the appliance is held in place primarily due to a tight fit.

35. The oral therapeutic appliance of claim 33, wherein the pooling reservoirs are located on the oral therapeutic appliance corresponding to the oral soft tissue at or near the patient's gingival margin.

36. The oral therapeutic appliance of claim 33, wherein the pooling reservoirs are located on the oral therapeutic appliance corresponding to the oral soft tissue at or near the patient's palate.

37. The oral therapeutic appliance of claim 33, wherein the pooling reservoirs are located on the oral therapeutic appliance corresponding to the patient's sublingual oral soft tissue.

38. The oral therapeutic appliance of claim 33, wherein the pooling reservoirs are located on the oral therapeutic appliance corresponding to the oral soft tissue at or near the patient's palate and to the patient's sublingual oral soft tissue.

39. The oral therapeutic appliance of claim 33, wherein the medicament to be delivered is selected from the group consisting of antibiotic compounds, antimicrobial compounds, antiviral compounds, antifungal compounds, anesthetic compounds, analgesic compounds, steroids and combinations thereof.

40. The oral therapeutic appliance of claim 39, wherein the antibiotic compound to be delivered comprises tetracycline.

41. The oral therapeutic appliance of claim 39, wherein the antimicrobial compound to be delivered comprises chlorhexidine.

42. The oral therapeutic appliance of claim 33, wherein the medicament to be delivered is insulin, chlorhexidine, fluoride, metronidazole, minocycline, tetracycline, peroxide, or combinations thereof.

43. The oral therapeutic appliance of claim 33, wherein the rein the sheet material is a thermoplastic sheet.

44. The oral therapeutic appliance of claim 43, wherein the thermoplastic sheet has a thickness of from about 0.04 inches to about 0.2 inches.

45. The oral therapeutic appliance of claim 44, wherein the thermoplastic sheet has a thickness of about 0.06 inches.

46. The oral therapeutic appliance of claim 43, wherein at least a portion of the molded sheet material extends to the patient's muco-gingival junction.

47. The oral therapeutic appliance of claim 33, wherein at least a portion of the molded sheet material extends at least 2 mm beyond the patient's gingival margin.

48. The oral therapeutic appliance of claim 33, wherein at least a portion of the molded sheet material extends at least 2 mm buccally beyond the patient's gingival margin.

49. The oral therapeutic appliance of claim 33, wherein at least a portion of the molded sheet material extends at least 2 mm lingually beyond the patient's gingival margin.

50. The oral therapeutic appliance of claim 33, wherein at least a portion of the molded sheet material extends at least 5 mm beyond the patient's gingival margin.

51. The oral therapeutic appliance of claim 33, wherein at least a portion of the molded sheet material extends at least 5 mm buccally beyond the patient's gingival margin.

52. The oral therapeutic appliance of claim 33, wherein at least a portion of the molded sheet material extends at least 5 mm lingually beyond the patient's gingival margin.

53. A method of delivering medicament to a patient's oral soft tissue comprising:
(a) covering at least a portion of the patient's teeth, edentulous areas or both, and adjacent buccal and lingual soft tissues with a molded contoured oral therapeutic appliance that is configured to extend beyond the patient's gingival margin, the oral therapeutic appliance further comprising one or more pooling reservoirs for holding a precise volume of medicament to be delivered to the oral soft tissue, wherein said one or more pooling reservoirs allow movement of the medicament;

(b) placing the medicament to be delivered within the oral therapeutic delivery appliance;
(c) positioning the oral therapeutic appliance over the teeth, edentulous areas or both in the area where the medicament is to be delivered such that at least a portion of the medicament is able to contact the soft tissue; and
(d) maintaining the oral therapeutic appliance in position for a sufficient time to allow a therapeutically effective amount of the medicament to be absorbed by the soft tissue.

54. The method of claim 53, wherein the pooling reservoirs are located on the oral therapeutic appliance corresponding to the oral soft tissue at or near the patient's gingival margin.

55. The method of claim 53, wherein the pooling reservoirs are located on the oral therapeutic appliance corresponding to the oral soft tissue at or near the patient's palate.

56. The method of claim 53, wherein the pooling reservoirs are located on the oral therapeutic appliance corresponding to the patient's sublingual oral soft tissue.

57. The method of claim 53, wherein the pooling reservoirs are located on the oral therapeutic appliance corresponding to the oral soft tissue at or near the patient's palate and to the patient's sublingual oral soft tissue.

58. The method of claim 53, wherein the oral therapeutic appliance is maintained in position primarily due to a tight fit.

59. The method of claim 53, wherein the medicament to be delivered is selected from the group consisting of antibiotic compounds, antimicrobial compounds, antiviral compounds, antifungal compounds, anesthetic compounds, analgesic compounds, steroids and combinations thereof.

60. The method of claim 59, wherein the antibiotic compound to be delivered comprises tetracycline.

61. The method of claim 59, wherein the antimicrobial compound to be delivered comprises chlorhexidine.

62. The method of claim 53, wherein the medicament to be delivered is insulin, chlorhexidine, fluoride, metronidazole, minocycline, tetracycline, peroxide, or combinations thereof.

63. A method of forming an oral therapeutic appliance comprising:
(a) forming an impression of a patient's mouth that registers at least a portion of the patient's teeth, edentulous areas or both, and surrounding gingival tissue;
(b) using the impression to form a stone cast model of the mouth;
(c) placing a precise volume of flowable composite on the stone cast model at a region corresponding to the patient's oral soft tissue;
(d) curing the flowable composite on the stone cast; and
(e) molding a thermoplastic sheet over the stone cast such that said cured flowable composite forms one or more pooling reservoirs within the oral therapeutic appliance for holding a precise volume of medicament to be delivered to the oral soft tissue, wherein said one or more pooling reservoirs allow movement of a medicament.

64. The method of claim 63, wherein the impression registers the patient's gingival areas.

65. The method of claim 63, wherein the impression extends at least up to 5 mm beyond the patient's gingival margin.

66. The method of claim 63, wherein the impression extends beyond the patient's muco-gingival junction.

67. The method of claim 63, wherein the flowable composite is placed on the stone cast at a region corresponding to the oral soft tissue at or near the patient's gingival margin.

68. The method of claim 63, wherein the flowable composite is placed on the stone cast at a region corresponding to the oral soft tissue at or near a patient's palate.

69. The method of claim 63, wherein the flowable composite is placed on the stone cast at a region corresponding to the patient's sublingual oral soft tissue.

70. The method of claim 63, wherein the flowable composite is placed on the stone cast at a region corresponding to the oral soft tissue at or near a patient's palate and to the patient's sublingual oral soft tissue.

71. The method of claim 63, wherein, at least one of the regions where the flowable composite is placed has a width of from about 1 mm to about 5 mm.

72. The method of claim 63, wherein at least one of the regions where the flowable composite is placed has a width of from about 1 mm to about 3 mm.

73. The method of claim 63, wherein the flowable composite extends substantially the length of the gingival margin.

74. The method of claim 63, wherein thermoplastic sheet has a thickness of from about 0.04 inches to about 0.2 inches.

75. The method of claim 74, wherein the thermoplastic sheet has a thickness of about 0.06 inches.

76. The method of claim 75, wherein at least a portion of the molded thermoplastic sheet extends to a patient's mucogingival junction.

77. The method of claim 63, wherein at least a portion of the molded thermoplastic sheet extends at least 2 mm beyond a patient's gingival margin.

78. The method of claim 63, wherein at least a portion of the molded thermoplastic sheet extends at least 2 mm buccally beyond a patient's gingival margin.

79. The method of claim 63, wherein at least a portion of the molded thermoplastic sheet extends at least 2 mm lingually beyond a patient's gingival margin.

80. The method of claim 63, wherein the flowable composite on the stone cast is light cured.

81. The method of claim 63, wherein the flowable composite is a high melting wax, molding clay, acrylic or other polymerizable material.

82. The method of claim 63, wherein at least a portion of the molded thermoplastic sheet extends at least 5 mm beyond the patient's gingival margin.

83. The method of claim 63, wherein at least a portion of the molded thermoplastic sheet extends at least 5 mm buccally beyond the patient's gingival margin.

84. The method of claim 63, wherein at least a portion of the molded thermoplastic sheet extends at least 5 mm lingually beyond the patient's gingival margin.

85. The method of claim 63, wherein the volume of medicament held by the one or more pooling reservoirs formed within the oral therapeutic appliance is determined by the volume of flowable composite placed on the stone cast.

* * * * *

UNITED STATES PATENT AND TRADEMARK OFFICE
CERTIFICATE OF CORRECTION

PATENT NO.     : 6,626,669 B2
DATED          : September 30, 2003
INVENTOR(S)    : Zegarelli It is certified that error appears in the above-identified patent and that said Letters Patent is hereby corrected as shown below:

Title page,
Item [56], References Cited, OTHER PUBLICATION, in "Arakawa, H., et al." reference, change "fluroide" to -- fluoride --.

Column 1,
Line 31, after "Topical medications for orofacial neuropathic pain:" italicize -- a review --.

Column 2,
Line 24, change "it's" to -- its --.

Column 4,
Line 8, change "former" to -- formerly --.

Column 6,
Lines 34 and 41, change "systematic antibiotics" to -- systemic antibiotics --.

Column 8,
Line 48, insert -- , -- after "claim 29".
Line 62, insert -- , -- after "claim 33".

Column 9,
Line 29, delete "the rein".

Signed and Sealed this

Eleventh Day of May, 2004

JON W. DUDAS
*Acting Director of the United States Patent and Trademark Office*